(12) United States Patent
Aptaker et al.

(10) Patent No.: US 9,305,742 B2
(45) Date of Patent: Apr. 5, 2016

(54) METHOD AND DEVICE FOR BUNCHING A BEAM OF CHARGED PARTICLES

(75) Inventors: Peter Simon Aptaker, Wantage (GB); Paul Beasley, Abingdon (GB); Oliver Heid, Erlangen (DE)

(73) Assignee: SIEMENS AKTIENGESELLSCHAFT (DE)

( * ) Notice: Subject to any disclaimer, the term of this patent is extended or adjusted under 35 U.S.C. 154(b) by 0 days.

(21) Appl. No.: 14/397,245

(22) PCT Filed: May 31, 2012

(86) PCT No.: PCT/EP2012/060273
§ 371 (c)(1),
(2), (4) Date: Nov. 20, 2014

(87) PCT Pub. No.: WO2013/178275
PCT Pub. Date: Dec. 5, 2013

(65) Prior Publication Data
US 2015/0126797 A1    May 7, 2015

(51) Int. Cl.
*H01J 37/00* (2006.01)
*H01J 37/147* (2006.01)
*H05H 7/18* (2006.01)
*H05H 7/22* (2006.01)
*A61N 5/10* (2006.01)
*H05H 7/02* (2006.01)

(52) U.S. Cl.
CPC ........... *H01J 37/1471* (2013.01); *A61N 5/1077* (2013.01); *H05H 7/18* (2013.01); *H05H 7/22* (2013.01); *H05H 2007/025* (2013.01)

(58) Field of Classification Search
CPC ..... H01J 37/1471; A61N 5/1077; H05H 7/22; H05H 5/02

USPC ................................ 250/396 R, 492.1, 492.3
See application file for complete search history.

(56) References Cited

U.S. PATENT DOCUMENTS

| 2,606,291 | A |   | 8/1952 | Wilson |            |
| 4,667,111 | A | * | 5/1987 | Glavish et al. | 250/492.2 |
| 5,719,478 | A | * | 2/1998 | Washio et al. | 315/500 |

OTHER PUBLICATIONS

Niki K. et al; "Design and Test of 2-4MHz Sawtooth-wave Pre-Buncher for 26MHz-RFQ"; IPAC '10 Proceedings, Kyoto; pp. 3903-3905; XP002695191; 2010; JP.
Bylinski Y. et al; "A Triple Gap Resonator Design for the separated Function DTL at Triumf"; PAC 1997 Proceedings, Vaoncouver; pp. 1135-1137; XP002695192; 1997; CA.
Fong K. et al; "Sawtooth Wave Generation for Pre-Buncher Cavity in ISAC"; PAC 1997 Proceedings Vancouver; pp. 3057-3059; XP002695193; 1997; CA.

(Continued)

*Primary Examiner* — Michael Maskell
(74) *Attorney, Agent, or Firm* — Schmeiser Olsen & Watts LLP

(57) ABSTRACT

A method for packetizing a beam-charged particle, in which the particles pass through an electric field in a device is provided. The device includes an annular shaped central electrode which, in the direction of the beam, is arranged between a first outer electrode and a second outer electrode. A time-dependent electric voltage signal is applied to the central electrode, the temporal course thereof being selected such that particles inside the device undergo a position-dependent speed modification. The course of the speed modification is approximately sawtooth-shaped in the direction of the beam. An associated device is also provided.

9 Claims, 5 Drawing Sheets

(56) References Cited

OTHER PUBLICATIONS

Ostrumov P. N. Eta L; "Beam Test of a Grid-Less Multi-Harmonic Buncher"; PAC '07 Proceedings, Albuquerque, New Mexico; pp. 2242-2244; XP002695194; 2007; US.

Schmor P. W.; "Initial Commissioning of the ISAC RIB Facility"; PAC 1999 Proceedings, New York; pp. 508-512; XP002695195; 1999; US.

Chabert A. et al; "The linear buncher of SPIRAL Beam test of a prototype"; Nuclear Instruments&Methods in Physics Resarch, Section a: Accelerators, Spectrometers, Detectors, and Associated Equipment, Elsevier BV Noth-Holland; vol. 423; No. 1; pp. 7-15; ISSN: 0168-9002; DOI: 10.1016/S0168-9002(98)01224-8; XP004160829; 1999; NL; Feb. 21, 1999.

International Search Report on PCT Application No. PCT/EP2012/060273, mailed on Apr. 24, 2014.

* cited by examiner

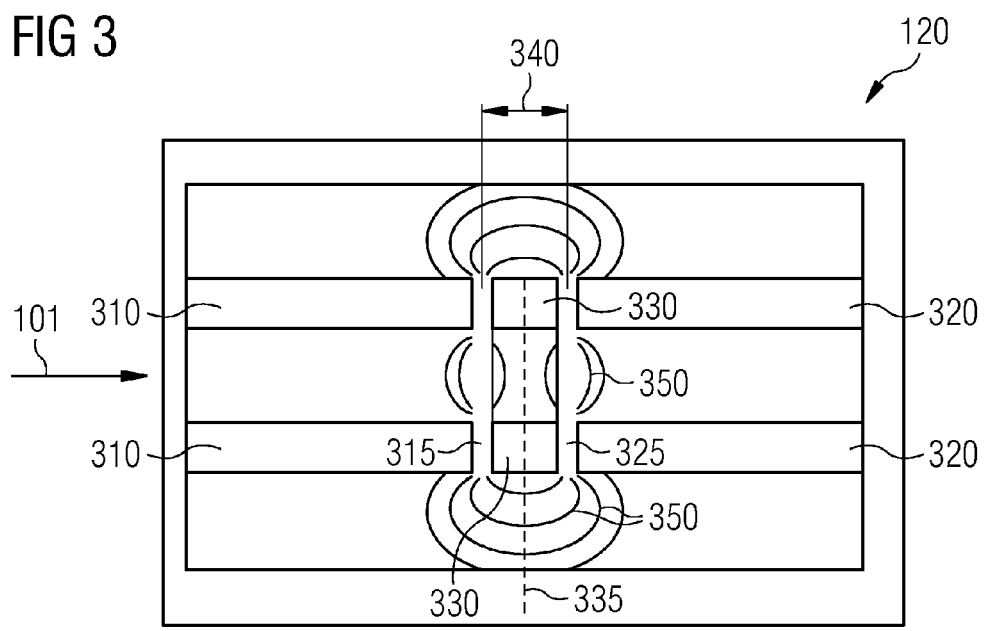
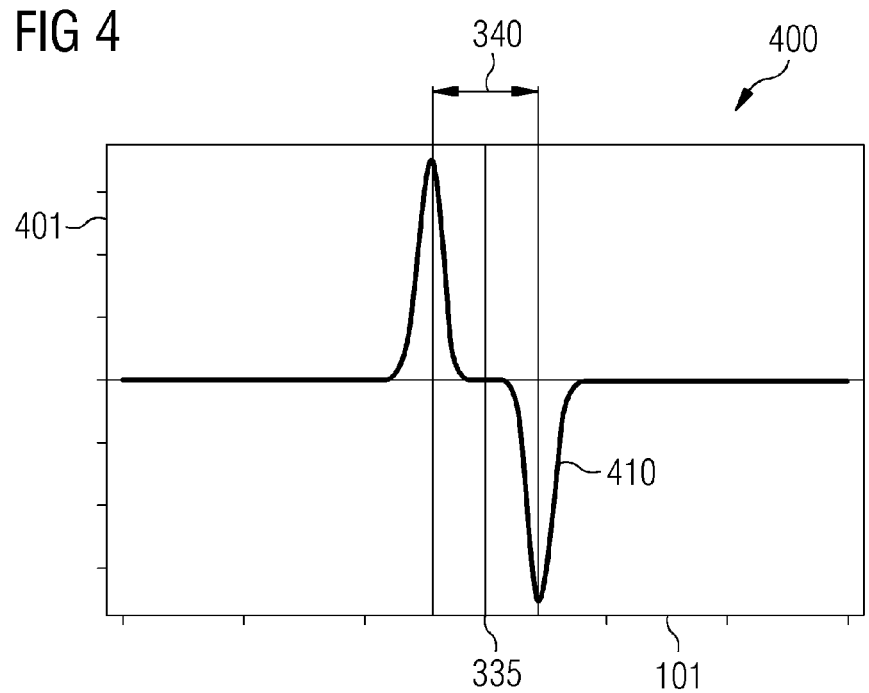

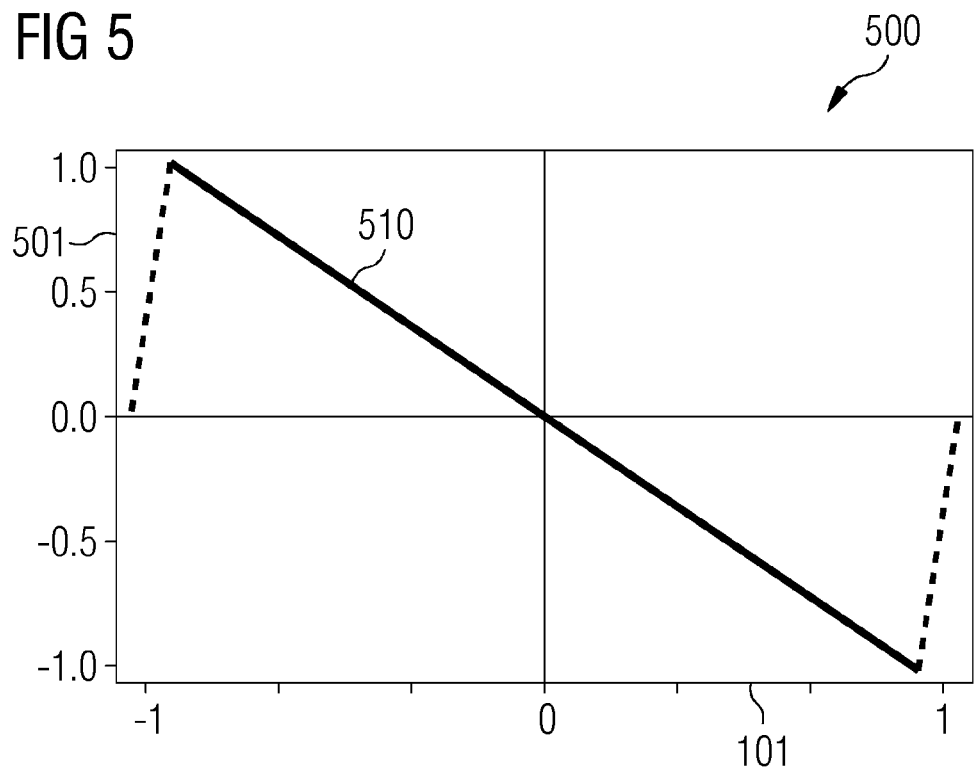
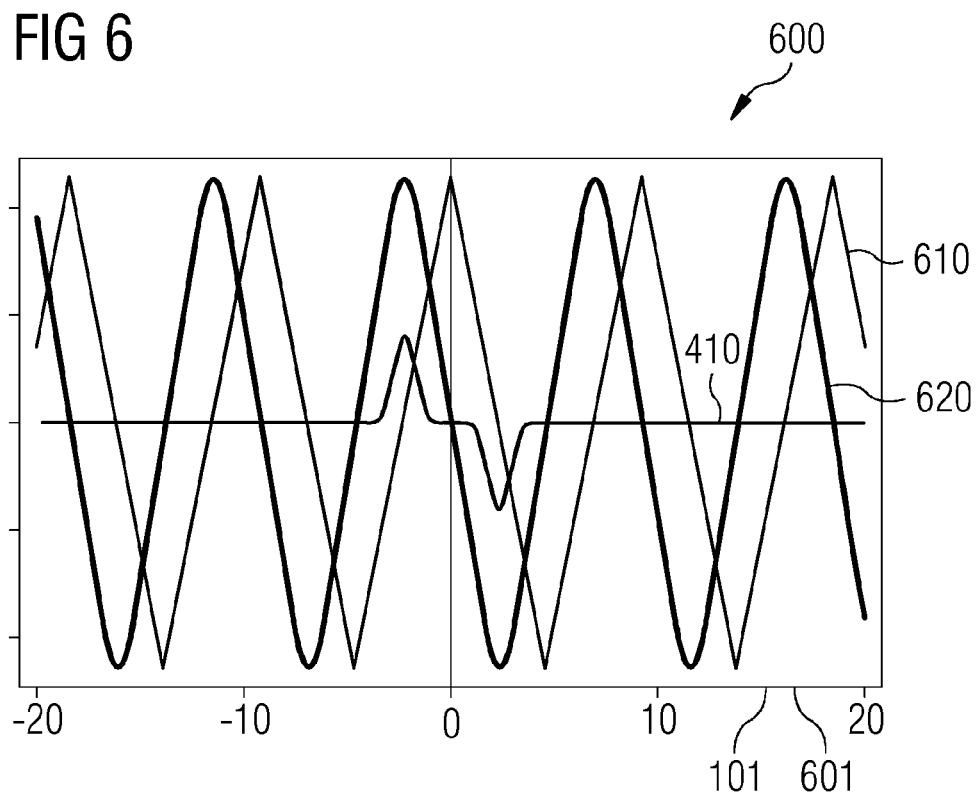

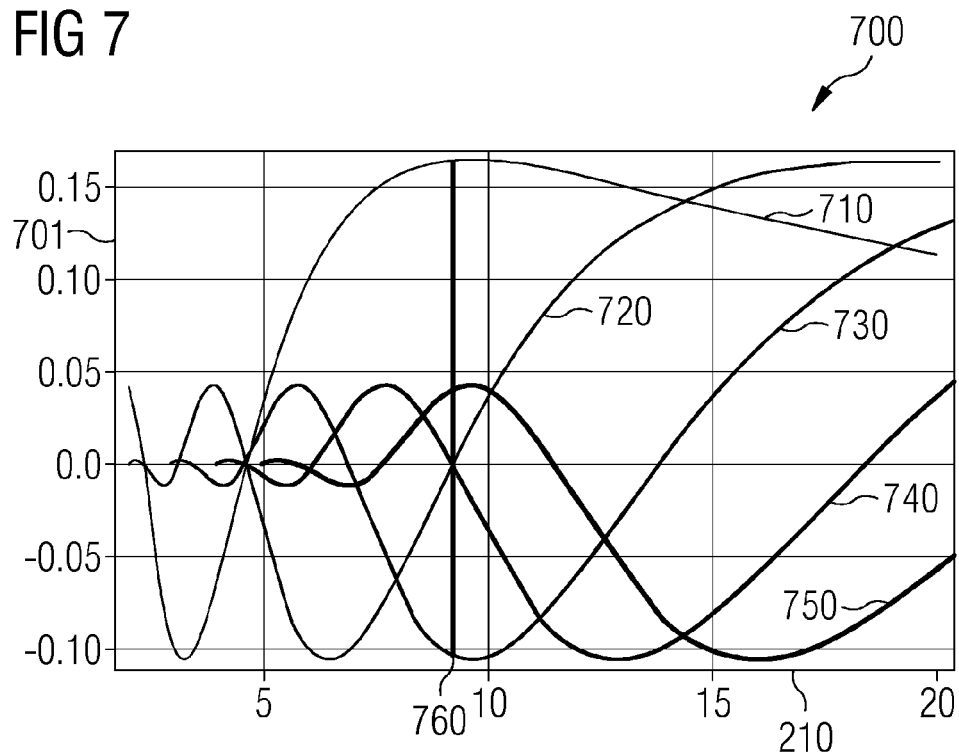
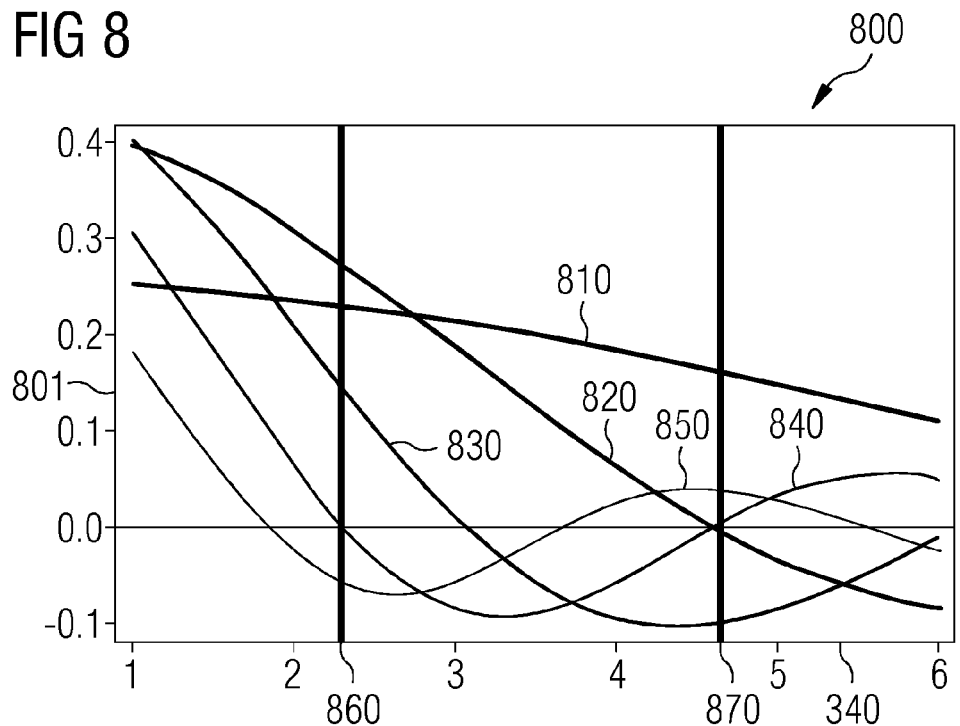

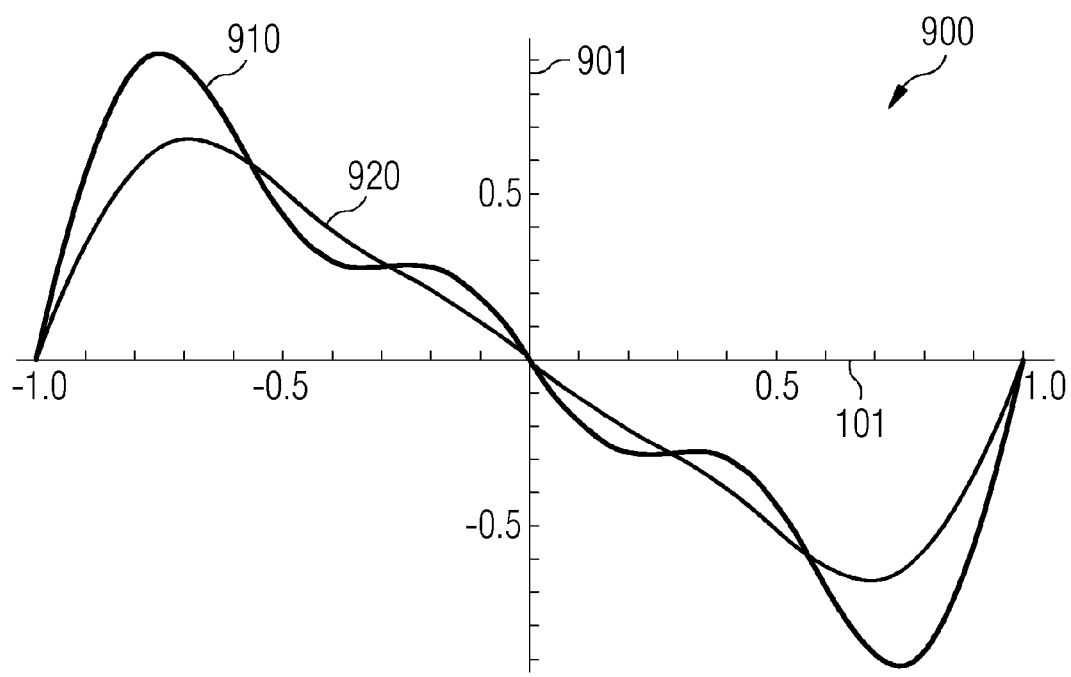

METHOD AND DEVICE FOR BUNCHING A BEAM OF CHARGED PARTICLES

CROSS-REFERENCE TO RELATED APPLICATIONS

This application claims priority to PCT Application No. PCT/EP2012/060273 having a filing date of May 31, 2012, the entire contents of which are hereby incorporated by reference.

FIELD OF TECHNOLOGY

The following relates to a method for bunching a beam of charged particles, a device for bunching a beam of charged particles and an instrument for performing particle therapy.

BACKGROUND

Accelerated charged particles, for example electrons and protons, are used for a multitude of technical, scientific and medical purposes. The generation of such particles using particle sources and the acceleration thereof using particle accelerators is known.

Particle sources often generate continuous beams of charged particles. Some particle accelerators, for example RF linear accelerators, are not suitable for accelerating continuous particle beams. Therefore, it is necessary for the particle beams to be bunched by means of a bunching device (buncher), i.e. to subdivide these beams into discrete particle bunches.

The prior art, for example of U.S. Pat. No. 5,719,478, has disclosed various bunching devices for bunching continuous particle beams. However, these known devices are disadvantageous in that they result in non-ideal bunching in the case of small beam currents, in which a space charge distribution does not influence the bunching process.

SUMMARY

An aspect relates to an improved method for bunching a beam of charged particles. A further aspect relates to providing an improved device for bunching a beam of charged particles. A further aspect includes providing an instrument for performing particle therapy.

In a method according to embodiments the invention for bunching a beam of charged particles, the particles pass through an electric field in a device. Here, the device comprises a ring-shaped central electrode which is disposed between a first outer electrode and a second outer electrode in a beam direction. A time-dependent electric voltage signal is applied to the central electrode, the electric profile of which electric voltage signal is selected in such a way that particles situated within the device experience a position-dependent change in velocity, the profile of the change in velocity being approximately sawtooth in the beam direction. Advantageously, a sawtooth change in velocity of the particles in the beam direction leads to very high quality bunching with good bunch properties, both in the case of partial and complete bunching.

In a preferred embodiment of the method, the electric voltage signal has an approximately triangular time profile. Advantageously, this constitutes a suitable option of obtaining a change in velocity with an approximately sawtooth profile in the beam direction.

In a development of the method, a first gap is formed between the first outer electrode and the central electrode and a second gap is formed between the central electrode and the second outer electrode. Here, the centers of the first gap and of the second gap have a fixed gap distance from one another. The electric voltage signal has a set excitation frequency. The particles have a set velocity prior to passing through the device. In the process, a bunch distance emerges as a quotient of the speed and the excitation frequency. The excitation frequency is selected in such a way that at least the three lowest Fourier components of the position-dependent change in velocity differ from zero. Advantageously, what then emerges from this is an expedient approximation of the profile of the change in velocity in the beam direction to a sawtooth form.

In one embodiment of the method, the excitation frequency is selected in such a way that the bunch distance is four times the size of the gap distance. Advantageously, then at least the three lowest Fourier components differ from zero.

In one embodiment of the method, the particles have a nonrelativistic velocity.

In one embodiment of the method, the outer electrodes are grounded. Advantageously, what emerges from this is a potential difference between the outer electrodes and the central electrode.

A device according to embodiments of the invention for bunching a beam of charged particles comprises a ring-shaped central electrode which is disposed between a first outer electrode and a second outer electrode in a beam direction. Here, a first gap is formed between the first outer electrode and the central electrode and a second gap is formed between the central electrode and the second outer electrode. Here, the centers of the first gap and of the second gap have a fixed gap distance from one another. The device is moreover embodied to be operated according to a method of the type mentioned above. Advantageously, the device is then suitable for subdividing a particle beam into bunches with excellent bunch properties.

An instrument according to embodiments of the invention for performing particle therapy comprises a device of the type set forth above. Advantageously, the particle therapy can then be performed with bunches of charged particles.

BRIEF DESCRIPTION

Some of the embodiments will be described in detail, with reference to the following figures, wherein like designations denote like members, wherein:

FIG. 3 shows a schematic illustration of an embodiment of a bunching device;

FIG. 4 shows a schematic illustration of an axial field distribution within the bunching device;

FIG. 5 shows a schematic illustration of an ideal field distribution;

FIG. 6 shows a schematic illustration of a real field distribution;

FIG. 7 shows a first Fourier decomposition;

FIG. 8 shows a second Fourier decomposition; and

FIG. 9 shows an optimized field distribution.

DETAILED DESCRIPTION

Figure 1:
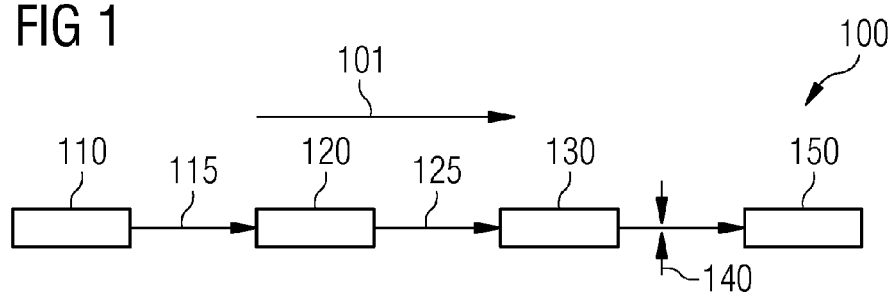
FIG. 1 shows a schematic block diagram of an embodiment of a particle therapy instrument.

FIG. 1 shows a schematic block diagram of a particle therapy instrument 100. The particle therapy instrument 100 serves as an example of an instrument in which a bunching device can be used. However, bunching devices according to embodiments of the invention can also be used in a multiplicity of further instruments.

The particle therapy instrument 100 can be used for performing particle therapy on a patient. During particle therapy, a diseased body location of the patient is irradiated with charged particles. By way of example, the charged particles can be protons.

The particle therapy instrument 100 comprises an ion source 110, which emits a particle beam 115 of charged particles in a beam direction 101. By way of example, the ion source 110 can be a proton source. By way of example, the ion source 110 can generate particles with an energy of between 10 keV and 20 keV. The particles leave the ion source 110 in the beam direction 101 as a continuous particle beam 115.

Following the ion source 110 in the beam direction 101, the particle therapy instrument 100 comprises a bunching device 120. The bunching device 120 is provided for subdividing the continuous particle beam 115 into a sequence of discrete particle bunches 125. The bunching device 120 can also be referred to as a buncher. The bunching of subdividing of the particle beam 115 into particle bunches 125 can also be referred to as packetizing. The particle bunches 125 leave the bunching device 120 in the unchanging beam direction 101.

Following the bunching device 120 in the beam direction 101, the particle therapy instrument 100 comprises a deflection device 130. The deflection device 130 can serve for deflecting individual particle bunches 125 in relation to the beam direction 101. A stop 140 is disposed following the deflection device 130 in the beam direction 101. Depending on the strength of the deflection of the particle bunches 125 from the beam direction 101 by the deflection device 130, the particle bunches 125 may pass the stop 140 completely, only partly or not at all. Therefore, the combination of deflection device 130 and stop 140 may serve for selective filtering and/or thinning of individual particle bunches 125.

Following the stop 140 in the beam direction 101, the particle therapy instrument 100 comprises a particle accelerator 150. By way of example, the particle accelerator 150 can be a linear accelerator, preferably an RF linear accelerator. The particle accelerator 150 serves to accelerate the particle bunches 125 to a higher kinetic energy of e.g. 80 MeV to 250 MeV.

Figure 2:
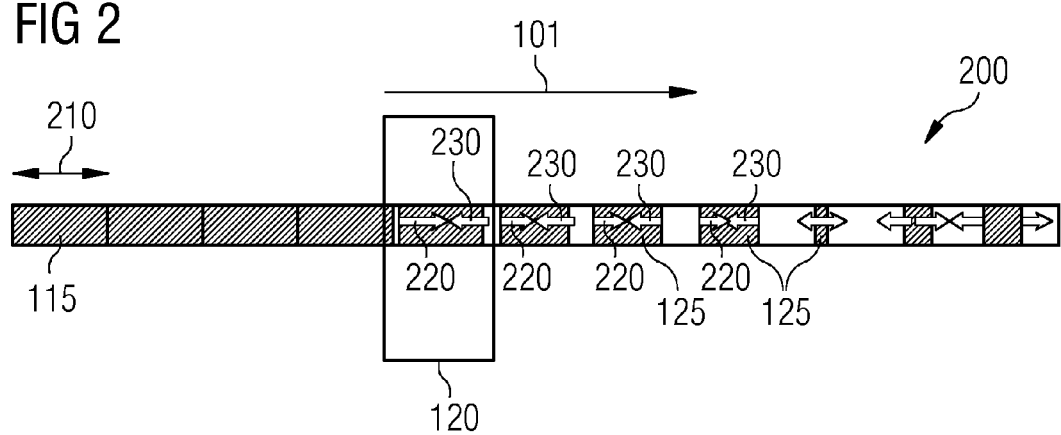
FIG. 2 shows a schematic of an embodiment a bunching scheme.

FIG. 2 shows a simplified illustration of a bunching scheme 200 in order to explain the bunching performed by the bunching device 120.

The continuous particle beam 115 runs into the bunching device 120 in the beam direction 101. By means of the bunching device 120, the particle beam 115 is subdivided into particle bunches 125, the centers of which have a bunch distance 210 in the beam direction 101. Here, the bunch distance 210 need not correspond to the length of the bunching device 120 in the beam direction 101.

The bunching is brought about by means of electric fields active within the bunching device 120, which electric fields influence the velocity of the particles of the particle beam 115 in the beam direction 101. Leading particles of each particle bunch 125 are decelerated in such a way that they obtain a reduced relative velocity 230. Late particles of each particle bunch 125 are accelerated such that they obtain an increased relative velocity 220. The reduction or increase in the relative velocity 220, 230 of a particle increases with distance thereof from the center of the particle bunch 125 thereof.

During the further movement of the particles in the beam direction 101, the particles toward the back of each particle bunch 125 in the beam direction 101 increasingly catch up with the leading particles of the respective particle bunch 125 as a result of their increased relative velocity 220. The leading particles of each particle bunch 125 are caught by the remaining particles of the particle bunch 125 during the further movement of the particles in the beam direction 101 due to their reduced relative velocity 230. The degree of bunching of the particle bunch 125 therefore increases in the beam direction 101 until maximum bunching is achieved at a point in the beam direction 101. From then on, the particle bunch 125 runs apart again during the further movement of the particles in the beam direction 101. In the particle therapy instrument 100, the point of maximal bunching of the particle bunches 125 can, for example, coincide with the location of the stop 140 or with the inlet of the particle accelerator 150.

FIG. 3 shows a schematic illustration of a section through the bunching device 120. In the beam direction 101, the bunching device comprises a first outer electrode 310, a central electrode 330 and a second outer electrode 320 in succession. The electrodes 310, 320, 330 in each case have a hollow cylindrical or tubular design. In the beam direction 101, the central electrode 330 is shorter than the outer electrodes 310, 320. Therefore, the central electrode 330 can also be referred to as ring-shaped. The particle beam 115 extends in the interior along the longitudinal axis of the tubular electrodes 310, 320, 330.

A first gap 315 is formed between the first outer electrode 310 and the central electrode 330. A second gap 325 is formed between the central electrode 330 and the second outer electrode 320. The gaps 315, 325 insulate the electrodes 310, 330, 320 from another electrically.

In the beam direction 101, the centers of the gaps 315, 325 have a gap distance 340 from one another. A center of the central electrode 330 in the beam direction 101 forms a center 335 of the bunching device 120.

During the operation of the bunching device 120, a time-dependent electric voltage is applied between the central electrode 330 and the outer electrodes 310, 320. Here, the outer electrodes 310, 320 preferably are at a common potential. By way of example, the outer electrodes 310, 320 may be grounded. A potential difference between the central electrode 330 and the outer electrodes 310, 320 causes the formation of an electric field, the equipotential lines 350 of which are depicted schematically in FIG. 3.

The field distribution in the beam direction 101 can approximately be described by Gaussian functions along the central axis (longitudinal axis) of the electrodes 310, 320, 330 of the bunching device 120. This is depicted schematically in the axial field distribution 400 in FIG. 4. The beam direction 101 in the region around the center 335 of the bunching device 120 is plotted on the horizontal axis of the graph in FIG. 4. The vertical axis of the graph in FIG. 4 shows the electric field strength 401 in the beam direction 101. A Gaussian approximation 410 approximates the profile of the electric field strength in the beam direction 101. The field distribution profile is Gaussian at each gap 315, 325. Therefore, the two Gaussian functions have the gap distance 340 from one another.

If a time-dependent electric voltage is applied to the central electrode 330 of the bunching device 120, the field distribution E(z) in the beam direction 101 (z), schematically depicted in FIG. 4, is modulated by the time-dependent electric field S(t) caused by the voltage applied to the central electrode 330. The instantaneous field $E_z$ in the beam direction 101 therefore emerges as a product of the axial field component E(z) and of the time-dependent field S(t):

$$E_z(z,t) = E(z)S(t).$$

A particle of the particle beam 115 entering the bunching device 120 in the beam direction 101 experiences a force in the beam direction 101 that is proportional to the instantaneous field $E_z$, and to its charge q. This results in a change in velocity $$v = -\frac{q}{m} E(z) * S(t),$$

which is proportional to a convolution of the axial field distribution E(z) and S(t). Here, the z-position in the beam direction 101, the velocity v of the particles of the particle beam 115 and the time t are linked by the bunch position $w=z-vt$. Here, m denotes the mass of the particle.

It would be most expedient if the convolution, and hence the change in velocity of the particles of the particle beam 115, were sawtooth-shaped in the beam direction 101. This would then result in a velocity variation which increases the further a particle is distanced from the center of the respective particle bunch 125. FIG. 5 shows a schematic graph of a change in velocity of the particles of the particle beam 115 emerging in the case of an appropriate field distribution 500. The bunch position w along the beam direction 101 is plotted on the horizontal axis. A relative change in velocity of the particles of the particle beam 115 is plotted on the vertical axis 501. An approximate sawtooth function 510 describes an approximately ideal relative change in velocity, which the particles of the particle beam 115 experience in order to obtain bunching with ideal bunching properties.

However, in practice the sawtooth function in FIG. 5 can only be achieved with difficulties. FIG. 6 shows a schematic graph of conditions prevailing in a real field distribution 600. The z position of the beam direction 101 and the bunch position w in the beam direction 101 and the path 601 traveled by the particles of the particle beam 115 in the time vt along the beam direction 101 are plotted on a horizontal axis of the graph depicted in FIG. 6. What is shown is the Gaussian approximation 410 of the axial field profile E(z). Moreover, the time profile of a voltage signal 610 applied to the central electrode 330 of the bunching device 120 is depicted. The voltage signal 610 has a triangular time profile. Moreover, FIG. 6 shows the resulting change in velocity 620 of the particles of the particle beam 115. It is possible to identify that a change in velocity 620 with a sinusoidal profile emerges despite the triangular time profile of the voltage signal 610. Therefore, the change in velocity 620 does not have an approximately sawtooth-shaped profile.

This can be explained by considering the Fourier coefficients:

$$\frac{\sqrt{\frac{2}{\pi}} e^{-\frac{2\pi^2 n^2 t1^2}{\lambda^2}} \sin\left(\frac{\pi n t2}{\lambda}\right)}{t2}.$$

Here, t2 is the gap distance 340, t1 is the width of the Gauss pulses of the Gaussian approximation 410, n is the order of the Fourier coefficients and $\lambda$ is the bunch distance 210 emerging as the quotient of the particle speed v and the excitation frequency f of the electric voltage signal S(t).

FIG. 7 shows the first five Fourier coefficients as a function of the bunch distance 210 in an exemplary fixed gap distance 340 of t2=4.6 in a first Fourier decomposition 700. Plotted on the horizontal axis of the graph depicted in FIG. 7 is the bunch distance 210 ($\lambda$). The amplitude of the respective Fourier coefficients is depicted on a vertical axis 701. The shown curves specify the profile of the first Fourier coefficient 710, of the second Fourier coefficient 720, of the third Fourier coefficient 730, of the fourth Fourier coefficient 740 and of the fifth Fourier coefficient 750.

In FIG. 7, a first bunch distance 760 of $\lambda=9.2=2$ t2 is marked. These are the parameters used in the illustration in FIG. 6. It can be seen that all even Fourier coefficients 720, 740, i.e. all harmonics, are filtered out in the first bunch distance 760. This is the reason for the sinusoidal profile of the change in velocity 620 in FIG. 6.

FIG. 8 shows a further Fourier decomposition 800. This time, the gap distance 340 (t2) is plotted on the horizontal axis. The bunch distance 210 is $\lambda=9.2$. A vertical axis 801 shows the amplitudes of the Fourier coefficients. Curves depict the profile of the first Fourier coefficient 810, of the second Fourier coefficient 820, of the third Fourier coefficient 830, of the fourth Fourier coefficient 840 and of the fifth Fourier coefficient 850. Moreover, a first gap distance 860 of t2=2.3 and the second gap distance 870 of t2=4.6=½$\lambda$, as used in FIG. 7, are marked. While the second Fourier coefficient 820 and the fourth Fourier coefficient 840 are filtered out in the second gap distance 870, as was already explained above on the basis of FIG. 7, the first three Fourier coefficients 810, 820, 830 have amplitudes that differ from zero in the case of the reduced first gap distance 860 of t2=2.3=¼$\lambda$. Thus, if the bunch distance 210 is selected to be four times greater than the gap distance 340, at least the first three Fourier coefficients 810, 820, 830 have amplitudes that differ from zero.

FIG. 9 shows the emerging relative change in velocity of the particles of the particle beam 115 in a graph of an optimized field distribution 900. The beam direction 101 is plotted on the horizontal axis. The emerging relative change in velocity of the particles of the particle beam 115 is depicted on the vertical axis 901. A first approximation 910 of a sawtooth function emerges if the gap distance 340 and the bunch distance 210, as described above, are selected in such a way that at least the first three Fourier coefficients have amplitudes that differ from zero. If the amplitudes of the individual Fourier coefficients are additionally optimized, this results in a second approximation 920, which is even more similar to a sawtooth function.

Although the invention has been described and depicted in greater detail by means of the preferred exemplary embodiment, the invention is not restricted by the disclosed examples. Other variations may be derived therefrom by a person skilled in the art without departing from the scope of protection of the invention.

The invention claimed is:

1. A method for bunching a beam of charged particles, wherein the charged particles pass through an electric field in a device, wherein the device comprises a ring-shaped central electrode which is disposed between a first outer electrode and a second outer electrode in a beam direction, wherein a time-dependent electric voltage signal is applied to the ring-shaped central electrode, a time profile of which electric voltage signal is selected in such a way that particles situated within the device experience a position-dependent change in velocity, wherein a profile of the change in velocity is approximately sawtooth in the beam direction;

wherein a first gap is formed between the first outer electrode and the central electrode and a second gap is formed between the central electrode and the second outer electrode, wherein the centers of the first gap and of the second gap have a fixed gap distance from one another, wherein the time-dependent electric voltage signal has an excitation frequency, wherein the charged particles have a set velocity prior to passing through the device, wherein a bunch distance emerges as a quotient of the speed and the excitation frequency, wherein the excitation frequency is selected in such a way that at least the three lowest Fourier components of the position-dependent change in velocity differ from zero.

2. The method as claimed in claim 1, wherein the time-dependent electric voltage signal has an approximately triangular time profile.

3. The method as claimed in claim 1, wherein the excitation frequency is selected in such a way that the bunch distance is four times the size of the gap distance.

4. The method as claimed in claim 1, wherein the first outer electrode and the second outer electrode are grounded.

5. A device for bunching a beam of charged particles, comprising a ring-shaped central electrode which is disposed between a first outer electrode and a second outer electrode in a beam direction, wherein a time-dependent electric voltage signal is applied to the ring-shaped central electrode, and a time profile of the time-dependent electric voltage signal has a profile of a positioned-dependent change in velocity which is approximately sawtooth in the beam direction;

wherein a first gap is formed between the first outer electrode and the central electrode and a second gap is formed between the ring-shaped central electrode and the second outer electrode, wherein the centers of the first gap and of the second gap have a fixed gap distance from one another;

wherein the time-dependent electric voltage signal has an excitation frequency, and the charged particles have a set velocity prior to passing through the device;

wherein a bunch distance emerges as a quotient of a speed and the excitation frequency, wherein the excitation frequency has at least the three lowest Fourier components of the position-dependent change in velocity which differ from zero.

6. An instrument for performing particle therapy using the device as claimed in claim 5.

7. The method of claim 1, wherein the device is a bunching device.

8. The method of claim 1, wherein the device subdivides the beam into a sequence of discrete particles bunches, further wherein leading particles of each particle bunch of the sequence of discrete particle bunches obtain a reduced velocity and late particles of each particle bunch of the sequence of discrete particle bunches obtain an increased relative velocity.

9. The method of claim 8, wherein the reduced velocity and the increased relative velocity increases with a distance from a center of each particle bunch of the sequence of discrete particle bunches.

* * * * *

UNITED STATES PATENT AND TRADEMARK OFFICE
CERTIFICATE OF CORRECTION

PATENT NO. : 9,305,742 B2
APPLICATION NO. : 14/397245
DATED : April 5, 2016
INVENTOR(S) : Peter Simon Aptaker et al.

It is certified that error appears in the above-identified patent and that said Letters Patent is hereby corrected as shown below:

On the Title page, References Cited, Other Publications, Col. 2, line 5, of the printed patent, please change "Vaoncouver" to --Vancouver-- after Proceedings.

On the Title page 2, References Cited, Other Publications, Col. 1, line 3, of the printed patent, please change "Eta L" to --Et al.--.

On the Title page 2, References Cited, Other Publications, Col. 2, line 2, of the printed patent, please change "Resarch" to --Research-- after Physics.

Signed and Sealed this
Twenty-eighth Day of June, 2016

Michelle K. Lee
*Director of the United States Patent and Trademark Office*